(12) United States Patent
Boll et al.

(10) Patent No.: US 8,222,408 B2
(45) Date of Patent: Jul. 17, 2012

(54) PROCESS FOR PREPARING ACYL AMIDE COMPOUNDS

(75) Inventors: Matthias Boll, Köln (DE); Burkhard Koch, Köln (DE)

(73) Assignee: SALTIGO GmbH, Langenfeld (DE)

( * ) Notice: Subject to any disclaimer, the term of this patent is extended or adjusted under 35 U.S.C. 154(b) by 146 days.

(21) Appl. No.: 12/641,437

(22) Filed: Dec. 18, 2009

(65) Prior Publication Data

US 2010/0222578 A1 Sep. 2, 2010

(30) Foreign Application Priority Data

Dec. 23, 2008 (DE) .......................... 10 2008 062 905

(51) Int. Cl.
*C07D 265/36* (2006.01)
(52) U.S. Cl. ........................... 544/105; 560/21; 564/280
(58) Field of Classification Search ................... 544/105
See application file for complete search history.

(56) References Cited

U.S. PATENT DOCUMENTS 6,977,299 B2 * 12/2005 Munson et al. ............... 544/105

FOREIGN PATENT DOCUMENTS

| CN | 1861253 | 11/2006 |
|----|---------|---------|
| EP | 1283829 | 6/2007 |
| WO | 0190088 | 11/2001 |

OTHER PUBLICATIONS

Bhaumik (Canadian Journal of Chemistry (2003), 81(3), 197-198.
Han, et al. (Tetrahedron Letters (1985), 26(50), 6233-4).
Lu, et al. (Zhejiang Gongye Daxue Xuebao (2002), 30(5), 464-466).
Santra, et al. (Journal of Molecular Catalysis (1987)m 39(3), 279-92).
Hayakawa I., et al: "Synthesis and Antibacterial Activities of Substituted 7-oxo-2,3-dihydro-7H-pyridou1,2,3-de ¾ U1,4 ¾ benzoxazine-6-carboxylic acids", Chemical and Pharmaceutical Society of Japan, (Dec. 1, 1984), No. 12, pp. 4907-4913.
Smith A.J., et al.: "The Preparation of Skeletal Catalysts", Annual Review of Materials Research, Annual Reviews, Palo Alto, CA, US, (Aug. 1, 2005), pp. 127-135.
Mu Xuhong, et al.: "Amorphous Nickel Based Alloy Catalysts and Magnetically Stabilized Bed Hydrogenation Technology", China Petroleum Processing and Petrochemical Technology, CN, (Dec. 1, 2002), pp. 25-31.
European Search Report from co-pending Application EP09178920 dated Jan. 12, 2012, 8 pages.
Organikum, 21st edition, p. 627ff, Wiley VCH Weinheim, 2001.

* cited by examiner

*Primary Examiner* — Kahsay T Habte
(74) *Attorney, Agent, or Firm* — Michael A. Miller

(57) ABSTRACT

A process for preparing acyl amide compounds is described, in which a recrystallized o-nitrophenoxy carbonyl compound is hydrogenated with hydrogen gas in the presence of a nickel sponge metal catalyst with ring closure to form a benzoxazine, which is then reacted with an acyl halide to give the corresponding acyl amide compound.

7 Claims, 1 Drawing Sheet

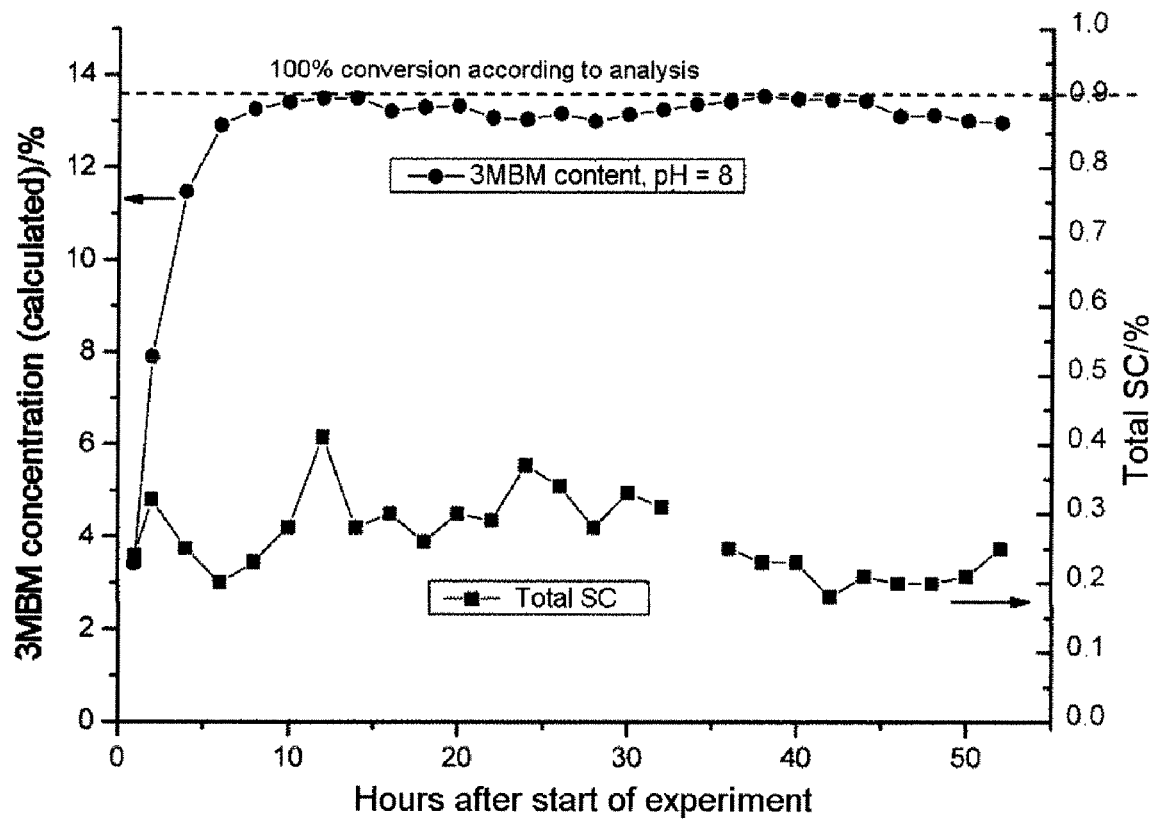

PROCESS FOR PREPARING ACYL AMIDE COMPOUNDS

BACKGROUND OF THE INVENTION

A process for preparing acyl amide compounds is described, in which a purified o-nitrophenoxy carbonyl compound is hydrogenated with hydrogen gas in the presence of a sponge metal catalyst with ring closure to form a benzoxazine, which is then reacted with an acyl halide to give the corresponding acyl amide compound.

Acyl amides are encountered in the dye industry and in agrochemical products, for example 4-(dichloroacetyl)-3,4-dihydro-3-methyl-2H-1,4-benzoxazine (benoxacor).

The preparation of benoxacor, a safener in the use of herbicides, is a three-stage process: in the first stage, o-nitrophenol is reacted with chloroacetone to give o-nitrophenoxyacetone; in the second stage, the compound is hydrogenated so as to obtain a benzoxazine, which is then acylated. This process is described in EP1283829.

The rate-determining and hence most expensive step in this process is the hydrogenation of the o-nitrophenoxy carbonyl compound, here a nitrophenoxy ketone, to the corresponding benzoxazine. In the process described in EP1283829, a noble metal catalyst attached to an activated carbon filter is used for this purpose. According to the present description, several disadvantages are associated with this process:

- firstly, it is a batchwise process which is associated with a low space-time yield and is therefore costly;
- in addition, a comparatively expensive catalyst is used, which additionally also has a high loading of a very valuable noble metal (of about 5% by weight of Pt);
- in addition, the catalyst used is purified to remove secondary components in a complex washing step after only about 10 g of nitro compound per gram of catalyst, which, as well as further prolonging the service life, also causes costs for the recycling and the disposal of the solvents used,
- in addition, the process proposed there gives rise to a series of secondary components, in particular the 3MBM dimer, which influences the purity of the end product and the yield.

The reduction of aromatic nitro groups with hydrogen to the corresponding amines as an unisolated intermediate, which is required in the second step, is performed globally on the industrial scale in the chemical industry. In principle, a whole series of catalysts is suitable for nitro reductions, starting from nickel or cobalt catalysts (in the form of the corresponding sponge metal catalysts (also known as skeletal catalysts) prepared from aluminium-nickel alloys by leaching, or else in fine distribution on support materials). Mixtures of nickel and other metals, for example iron, molybdenum, chromium (all likewise prepared by leaching from corresponding aluminium-metal alloys) are likewise suitable in principle.

These alloys can also be used for nitro reduction at low temperature in aqueous phase with addition of ammonium chloride, as reported by Bhaumik (Canadian Journal of Chemistry (2003), 81(3), 197-198).

In addition to these comparatively costly catalyst types, supported noble metal catalysts are also useful, for example platinum or palladium on activated carbon, whose reactivity, like that of the Raney catalysts, can also be attenuated in a controlled manner with the addition of ammonia or another amine or another catalyst poison. These catalysts have two disadvantages compared to the nickel sponge metal or cobalt sponge metal catalysts: firstly, they are generally more difficult to filter and the associated catalyst losses are greater; secondly, the purchase costs for noble metal catalysts are significantly higher.

Other means of reducing nitro groups, for instance the reduction with zinc, tin or iron in HCl proposed in Organikum (21$^{st}$ edition, p. 627 ff., Wiley VCH, Weinheim), play just as minor a role in the chemical industry as the reduction with, for example, hydrazine, as described, inter alia, by Han et al. (Tetrahedron Letters (1985), 26(50), 6233-4). Homogeneous catalysts based on noble metals have also already been mentioned for the reduction, for example by Sandra et al. (Journal of Molecular Catalysis (1987), 39(3), 279-92). In the examples specified above, moreover, only the nitro group on the aromatic ring was always hydrogenated; a further reductive amination was not considered here.

There is currently also the possibility of using metal catalysts on an inorganic support for reduction, for instance a copper catalyst in the presence of nickel and/or palladium on a silicate (CN1861253). Lu et al. (Zhejiang Gongye Daxue Xuebao (2002), 30(5), 464-466) also reported carbon nanotubes as support material.

The use of sponge metal catalysts is limited in particular by the temperature at which the hydrogenation can proceed: at excessively high temperatures, generally not only the nitro group but also, in an undesired manner, the aromatic ring is hydrogenated. This ring hydrogenation leads to yield losses and, associated with this, to higher costs.

It was an object of the present invention to discover a process for preparing acyl amide compounds which can be performed in a good space-time yield with only low formation of undesired by-products and with inexpensive catalysts.

A process which meets these requirements has now been found.

BRIEF SUMMARY OF THE INVENTION

The invention therefore provides a process for preparing an acyl amide compound of the general formula (I)

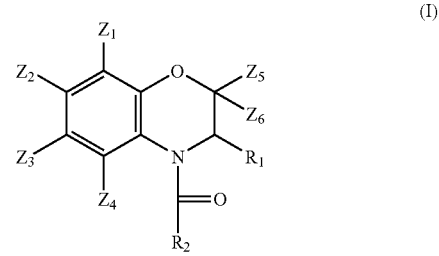

(I)

in which $R_1$ is hydrogen or a $C_1$-$C_8$-alkyl radical, $R_2$ is a dichloromethyl or trichloroethyl group, and $Z_1$ to $Z_6$ are each independently hydrogen or a $C_1$-$C_8$-alkyl radical, wherein
a) an o-nitrophenoxy carbonyl compound of the general formula (II)

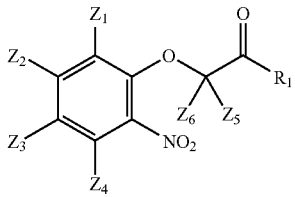

in which
R$_1$ and Z$_1$ to Z$_6$ are each as defined for formula (I)
is allowed to crystallize out of an organic solvent and removed,
b) the o-nitrophenoxy carboxyl compound is dissolved in a mixture of C$_1$-C$_3$-alcohol and an aromatic solvent,
c) the pH in this solution is set to a value between 6 and 11,
d) the o-nitrophenoxy compound of the formula (II) present in this solution is hydrogenated in the presence of a sponge metal catalyst with hydrogen gas with ring closure to give the benzoxazine compound of the formula (III)

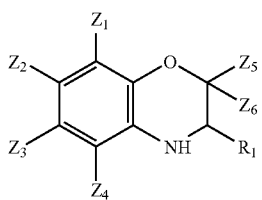

in which R$_1$ and Z$_1$ to Z$_6$ are each as defined for compounds of the formula (I), and then
e) the compound of the formula (III) is reacted with an acyl halide of the formula (IV)

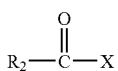

in which R$_2$ is as defined for compounds of the formula (I) and X is a halogen atom, in particular a chlorine atom, to give compounds of the formula (I).

BRIEF DESCRIPTION OF THE DRAWING

FIG. 1 illustrates the results of the hydrogenation of one embodiment of the present invention.

DETAILED DESCRIPTION OF THE INVENTION

The organic solvent in which the crystallization is performed in step a) may be an alcohol such as methanol, ethanol or isopropanol in a mixture with an aromatic solvent such as benzene, toluene or xylene. Preference is given to using isopropanol in a mixture with toluene in step a). The solid, which is obtained by crystallization down to −5° C. or lower, is then dissolved in step b), for example, in a methanol/toluene solvent mixture and adjusted in step c) to a pH between 6 and 11, for example by means of sodium hydroxide, before the hydrogenation is then performed in step d) at a hydrogen pressure of, for example, 220 bar.

For the hydrogenation of the o-nitrophenoxy carbonyl compound, it has been found, surprisingly, that this reaction can be performed in the presence of specific sponge metal catalysts virtually without side reactions (for example to give dimers of benzoxazine or to give partly hydrogenated compounds or to give other, undesired by-products) when a freshly crystallized or recrystallized o-nitrophenoxy carbonyl compound of the formula (II) is dissolved in a mixture of a C$_1$-C$_3$-alkocol, for example methanol, and an aromatic solvent, for example toluene, in which the pH has been set to a value between 6 and 11, preferably 7 and 10, more preferably 8-9.

The influence of the "pH" measured in the solvent mixture (the term "pH" should actually be replaced in the present case by a measured voltage against a reference electrode, since the measurement has been made in a nonaqueous system) has a surprisingly considerable influence on the formation of secondary components and the service life of the catalyst, as comparative experiments at other pH values show. Typically, the pH is measured with a glass pH electrode.

In general, the hydrogenation is performed in a solvent mixture of a C$_1$-C$_3$-alcohol such as methanol, ethanol or propanol in a mixture with an aromatic solvent such as toluene. The mixing ratios (in parts by weight) are between 1:100 aromatic solvent to alcohol up to 20:100 aromatic solvent to alcohol, such that, even taking account of the water of reaction which forms, monophasicity of the reaction mixture preferably (but not necessarily) remains guaranteed at the end of the reaction. Preference is given to a toluene/methanol mixture as a solvent for the hydrogenation with a mixing ratio of 9.7:100 toluene to methanol. Based on the description from EP1283829, it is, however, also possible to use solvent mixtures with a significantly higher proportion of toluene.

Moreover, the catalyst, under the selected experimental conditions, with >90 g of nitro compound per gram of catalyst (without intermediate washes of the catalyst), surprisingly exhibits a significantly longer service life than a noble metal catalyst.

The sponge metal catalysts used may be those which consist predominantly of nickel, but it is also possible to use iron-, aluminium- or molybdenum-doped sponge metal catalysts. Preference is given to using a molybdenum-doped catalyst, for example nickel sponge metal catalyst doped with 0.5 to 4% molybdenum, as obtainable, for example, under the AMPERKAT Ni—Mo 3706 trade name from H. C. Starck (Goslar, Germany).

The hydrogen pressure is typically between 100 and 240 bar, preferably 220 bar.

The reaction temperature in the hydrogenation in step d) may typically be in the range between 30 and 90° C., preferably 60° C.

The reaction time for the hydrogenation should be in the range between 0.3 and 5 hours, preferably 0.5 to 1.5 hours.

The hydrogenation can be performed batchwise or preferably continuously.

The acylation in step e) is known in principle to those skilled in the art. Typically, the solution from step d) is filtered to remove the catalyst and diluted with solvent, for example toluene, and then reacted with an acyl halogen of the formula (IV), such as preferably dichloroacetyl chloride (with R$_2$=dichloromethyl in formula (IV)) or trichloropropionyl chloride (with R$_2$=trichloroethyl in formula (IV)) in toluenic solution in the presence of aqueous sodium hydroxide solution. Preference is given to effecting the reaction with dichloroacetyl chloride (DCAC) at a pH of 2-3.5 at temperatures up to 80° C.

The process according to the invention is suitable for preparing all known acyl amides of the formula (I). Preference is given to preparing, by the process according to the invention, however, 4-(dichloroacetyl)-3,4-dihydro-3-methyl-2H-1,4-benzoxazine (benoxacor) from o-nitrophenoxyacetone. For this purpose, o-nitrophenoxyacetone, for example from the reaction of o-nitrophenol with chloroacetone (as specified in Example 1) is crystallized out and dissolved again, and then hydrogenated with hydrogen in the presence of doped sponge metal catalysts. The benzoxazine of the formula (III) where $R_1$=methyl and $Z_1$ to $Z_6$=hydrogen thus obtained from o-nitrophenoxyacetone is 3,4-dihydro-3-methyl-2H-1,4-benzoxazine (3-MBM is then reacted with DCAC to give 4-(dichloroacetyl)-3,4-dihydro-3-methyl-2H-1,4-benzoxazine (benoxacor), which is crystallized out of an isopropanol-toluene-water mixture and is added to herbicides as a safener or is used in combination with such herbicides).

The examples which follow are intended to further illustrate the invention, but without restricting its scope.

EXAMPLES

1$^{st}$ Stage: Preparation of o-nitrophenoxyacetone
(Precursor, Compound of the Formula (II))

a) In a nitrogen-purged 30 litre jacketed vessel with stirrer, two Pt100 sensors, pH electrode, earthed HC4 metal rod and reflux condenser, 3652 g of 98.3% o-nitrophenol (25.81 mol) were dissolved in 7910 g of toluene. To this solution were added 363 g of sodium bromide (3.53 mol), 2630 g (31.31 mol) of sodium hydrogencarbonate, 217 g of 70% tributylmethylammonium chloride solution (0.64 mol) in water. Subsequently, 2780 g of chloroacetone (30.05 mol, >96%) were added with stirring in a nitrogen atmosphere. The mixture was heated to 65° C. in a nitrogen atmosphere with stirring, which evolved a lot of $CO_2$.

b) Once the evolution of gas had almost stopped (after about six hours), 5456 g of water (at 55° C.) were metered in, then adjusted to a pH of 6.9-7 with 10% hydrochloric acid (~1396 g) with stirring. The aqueous phase was removed and the organic phase was washed with 5800 g of 10% sodium chloride solution (at 55° C.). The aqueous phase was removed again.

c) The organic phase was diluted with 4000 g of isopropanol and adjusted to a pH of 8.5 with 30% sodium hydroxide solution.

d) The reactor contents were cooled to −10° C. with stirring and the crystals were filtered off with suction and washed with about 1300 g of cold isopropanol. The yield was about 88% based on the nitrophenol used. The dried crystals are storage-stable.

2$^{nd}$ Stage: Preparation of
3,4-dihydro-3-methyl-2H-1,4-benzoxazine (3-MBM)

2624 g of o-nitrophenoxyacetone crystals (~98%) from the 1$^{st}$ stage, step d), were dissolved at room temperature in a mixture of 11 307 g of methanol and 1290 g of toluene at 40° C., in order to obtain an about 17.6% solution of nitrophenoxyacetone.

This solution was adjusted to a pH of 8-9 with 30% aqueous NaOH solution using a Schott H63 glass electrode. Only a little NaOH was needed for this purpose (less than 5 ml). The pH of the reactant solution changed over the course of time and had to be readjusted to a pH of 8-9 before further use. The reactant solution is not storage-stable in the present form (the solution should not be kept at a temperature of 40° C. for longer than a few hours), and the hydrogenation should be commenced rapidly.

The resulting solution was hydrogenated continuously. To this end, an autoclave was initially charged with the Amperkat Ni—Mo 3706 sponge metal catalyst in methanol, and the oNPA solution was metered in continuously under hydrogen pressure and with stirring. The reactor possessed a frit at the lid, through which the hydrogenated solution was forced out continuously by the fresh incoming solution.

Reaction conditions: 220 bar of hydrogen, reaction temperature 60° C. with a residence time of about 60-90 minutes. The space velocity was about 2 g of o-nitrophenoxyacetone per g of catalyst used and hour. The catalyst used was a nickel sponge metal catalyst from H. C. Starck, Amperkat Ni—Mo 3706 (exchange of the water under which the catalyst is stored for methanol). The yields in this step were 95+%; at least 100 g of nitrophenoxyacetone were converted per gram of theoretically dry catalyst. Good mixing was ensured by stirring. In order to prevent precipitation of the reactant solution, it was heated to 40° C.

In the course of the hydrogenation, samples were taken every two hours and analyzed by GC analysis. The relatively low concentration at the start of the reaction resulted from the presence of pure solvent together with the catalyst in the autoclave, into which the actual reaction solution was then metered. The theoretical value for a 100% conversion was about 13.5% 3MBM in the solution.

The results of the hydrogenation are shown in the table which follows (see also FIG. 1):

| Hours after start of experiment | 3MBM content in the solution/% | Secondary components/% based on 3MBM | Amount of oNPA metered in/g |
| --- | --- | --- | --- |
| 1 | 3.42 | 7.0 | 32 |
| 2 | 7.9 | 3.7 | 85 |
| 4 | 11.47 | 1.8 | 138 |
| 6 | 12.91 | 1.2 | 249 |
| 8 | 13.26 | 1.4 | 341 |
| 10 | 13.41 | 2.0 | 437 |
| 12 | 13.49 | 2.9 | 538 |
| 14 | 13.5 | 1.7 | 643 |
| 16 | 13.22 | 1.8 | 750 |
| 18 | 13.31 | 1.5 | 855 |
| 20 | 13.33 | 1.8 | 961 |
| 22 | 13.08 | 2.1 | 1070 |
| 24 | 13.04 | 2.8 | 1173 |
| 26 | 13.17 | 2.4 | 1280 |
| 28 | 13.01 | 2.0 | 1385 |
| 30 | 13.15 | 2.4 | 1477 |
| 32 | 13.25 | 2.3 | 1541 |
| 34 | 13.43 | 7.9 | 1619 |
| 36 | 13.43 | 1.8 | 1713 |
| 38 | 13.54 | 1.6 | 1790 |
| 40 | 13.48 | 1.6 | 1874 |
| 42 | 13.46 | 1.3 | 1948 |
| 44 | 13.45 | 1.5 | 2017 |
| 46 | 13.11 | 1.5 | 2115 |
| 48 | 13.14 | 1.5 | 2214 |
| 50 | 13.02 | 1.5 | 2314 |
| 52 | 12.97 | 1.8 | 2409 |

The red product solution obtained from the hydrogenation was filtered, and the filtrate was analyzed in order to determine the 3-MBM content.

The solution was then freed of the solvent in a jacketed vessel at bottom temperature 74° C. and pressure about 180 mbar; the residue which remained was a brown liquid which consisted essentially of 3MBM and water. Subsequently, operation was continued in a nitrogen atmosphere.

The dark brown liquid was, according to the analysis result, diluted with toluene at about 50° C. so as to form a 50% solution (about 3370 g of toluene). This solution was used for the acylation in the subsequent step for preparing 4-(dichloroacetyl)-3,4-dihydro-3-methyl-2H-1,4-benzoxazine (benzoxacor) with a yield of >90%.

Comparative Example a

Stage 2: Preparation of
3,4-dihydro-3-methyl-2H-1,4-benzoxazine (3-MBM) without Preceding Crystallization and without pH Adjustment and at Lower Pressure of 150 bar at Higher Temperature of 80° C.

Instead of the crystallized material from step 1d) used in step 2, the organic solution from step 1b), which has been diluted with 8500 g of methanol in order to ensure the solubility of the o-nitrophenoxyacetone at 40° C., is used in this comparative example.

A solution which contained about 20% o-nitrophenoxyacetone was thus obtained.

The resulting solution was hydrogenated continuously. To this end, an autoclave was initially charged with the Amperkat Ni—Mo 3706 sponge metal catalyst in methanol, and the oNPA solution was metered in continuously under hydrogen pressure and with stirring. The reactor possessed a frit at the lid, through which the hydrogenated solution was forced out continuously by the fresh incoming solution.

Reaction conditions: 150 bar of hydrogen, reaction temperature 80° C. with a residence time of about 60-90 minutes. The space velocity was about 2 g of o-nitrophenoxyacetone per g of catalyst used and hour. The catalyst used was a sponge metal catalyst from H. C. Starck, Amperkat Ni—Mo 3706 (exchange of the water under which the catalyst is stored for methanol). The yield was 90%; 42 g of nitrophenoxyacetone were converted per gram of theoretically dry catalyst. Thereafter, the hydrogenation had to be stopped owing to the massive formation of secondary components (in particular of the 3MBM dimer). Good mixing was ensured by stirring. In order to prevent precipitation of the reactant solution, it was heated to 40° C.

In the course of the hydrogenation, samples were taken every two hours and analyzed by GC analysis. The relatively low concentration at the start of the reaction resulted from the presence of pure solvent together with the catalyst in the autoclave, into which the actual reaction solution was then metered. The theoretical value for a 100% conversion was about 15.2% 3MBM in the solution.

The results of the hydrogenation are shown in the following table:

| Hours after start of experiment | 3MBM content in the solution/% | Total main secondary components/% based on 3MBM | Amount of oNPA metered in/g |
| --- | --- | --- | --- |
| 1  | 1.97  | 20.8 | 194 |
| 2  | 7.57  | 2.5  | 375 |
| 4  | 12.6  | 4.5  | 599 |
| 6  | 14.9  | 6.6  | 823 |
| 8  | 16.43 | 8.5  | 1799 |
| 10 | 16.46 | 5.5  | 2679 |
| 12 | 16.63 | 7.6  | 3532 |
| 14 | 16.52 | 8.0  | 3931 |
| 16 | 16.36 | 9.1  | 4178 |
| 18 | 16.13 | 9.7  | 4502 |
| 20 | 15.7  | 10.6 | 4806 |
| 22 | 14.89 | 9.0  | 5922 |
| 24 | 15    | 10.1 | 7287 |
| 26 | 14.54 | 10.5 | 8937 |
| 28 | 14.31 | 9.2  | 9227 |

The red product solution obtained from the hydrogenation was filtered, and the filtrate was analyzed in order to determine the 3MBM content.

The secondary components present in the resulting solution are at such a high level that the preparation of sufficiently pure benoxacor is impossible under these production conditions.

Comparative Example b

Stage 2: Preparation of
3,4-dihydro-3-methyl-2H-1,4-benzoxazine (3MBM) without Preceding Crystallization and without pH Adjustment and at a Pressure of 220 bar at 60° C.

Instead of the crystallized material from step 1d) used in step 2, the organic solution from step 1b), which has been diluted with 15 343 g of methanol in order to ensure the solubility of the o-nitrophenoxyacetone at 40° C., is used in this comparative example.

A solution which contained about 16.4% o-nitrophenoxyacetone was thus obtained. The resulting solution was hydrogenated continuously. To this end, an autoclave was initially charged with the Amperkat Ni—Mo 3706 sponge metal catalyst in methanol, and the oNPA solution was metered in continuously under hydrogen pressure and with stirring. The reactor possessed a frit at the lid, through which the hydrogenated solution was forced out continuously by the fresh incoming solution.

Reaction conditions: 220 bar of hydrogen, reaction temperature 60° C. with a residence time of about 60-90 minutes. The space velocity was about 2 g of o-nitrophenoxyacetone per g of catalyst used and hour. The catalyst used was a nickel sponge metal catalyst from H. C. Starck, Amperkat Ni—Mo 3706 (exchange of the water under which the catalyst is stored for methanol). The 3MBM yield was about 74%; more than 40 g of nitrophenoxyacetone were converted per gram of theoretically dry catalyst. Thereafter, the hydrogenation had to be stopped owing to the massive formation of secondary components (in particular of an unknown compound with mass 211 amu). Good mixing was ensured by stirring. In order to prevent precipitation of the reactant solution, it was heated to 40° C.

In the course of the hydrogenation, samples were taken every two hours and analyzed by GC analysis. The relatively low concentration at the start of the reaction resulted from the presence of pure solvent together with the catalyst in the autoclave, into which the actual reaction solution was then metered. The theoretical value for a 100% conversion was about 12.5% 3MBM in the solution.

The results of the hydrogenation are shown in the following table:

| Hours after start of experiment | 3MBM content in the solution/% | Total main secondary components/% based on 3MBM |
|---|---|---|
| 1 | 0.59 | 62.7 |
| 2 | 3.43 | 93.0 |
| 4 | 6.93 | 68.7 |
| 6 | 8.8 | 58.4 |
| 8 | 9.35 | 52.7 |
| 10 | 9.43 | 51.0 |
| 12 | 9.38 | 52.6 |
| 14 | 9.23 | 53.3 |
| 16 | 9.36 | 55.1 |
| 18 | 9.31 | 54.1 |
| 20 | 9.31 | 54.9 |
| 21 | 9.26 | 55.1 |

The red product solution obtained from the hydrogenation was filtered, and the filtrate was analyzed in order to determine the 3MBM content.

The secondary components present in the resulting solution are at such a high level that the preparation of sufficiently pure benzoxacor is impossible under these production conditions.

3$^{rd}$ Stage: 4-(dichloroacetyl)-3,4-dihydro-3-methyl-2H-1,4-benzoxazine (benoxacor)

3624 g of a 50% 3MBM solution from stage 2 were admixed with 2048 g of water and 53.2 g of 75% $H_3PO_4$.

A solution of 2519 g of 96% DCAC in 2120 g of toluene and a 30%© NaOH solution at 40-70° C. were then metered in simultaneously with stirring over 90 min such that the pH was kept between 2-3.

The emulsion was heated to 80° C. and stirred at 80° C. for a further 1 h.

The emulsion was then adjusted to pH 7 with 30% NaOH and hot-filtered with addition of cellulose.

The lower, aqueous phase was removed at 80° C. and the organic phase was freed of the solvent up to jacket temperature 95° C. and 250 mbar.

The residue was admixed at 80° C. with 8100 g of isopropanol and dissolved therein.

The solution was then admixed stepwise with a total of 12 000 g of water until it became cloudy. After cooling to room temperature, the crystals were filtered off with suction and washed with 15 000 kg of isopropanol/water mixture (10-50% by weight of isopropanol, preferably 10% by weight).

Finally, washing was also effected with 9000 g of water.

The yield was 91% based on the 3MBM used. The benzoxacor thus obtained exhibited, when analyzed, a content of >99.8%.

What is claimed is:

1. Process for preparing an acyl amide compound of formula (I)

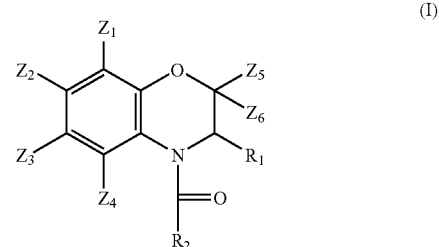

(I)

in which $R_1$ is hydrogen or a $C_1$-$C_8$-alkyl radical, $R_2$ is a dichloromethyl or trichloroethyl group, and $Z_1$ to $Z_6$ are each independently hydrogen or a $C_1$-$C_8$-alkyl radical, wherein a) an o-nitrophenoxy carbonyl compound of formula (II)

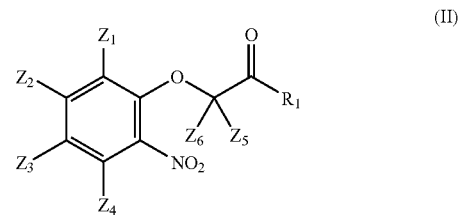

(II)

in which $R_1$ and $Z_1$ to $Z_6$ are each as defined for formula (I)

is allowed to crystallize out of an organic solvent and removed, b) the o-nitrophenoxy carboxyl compound is dissolved in a mixture of $C_1$-$C_3$-alcohol and an aromatic solvent, c) the pH in this solution is set to a value between 6 and 11, d) the o-nitrophenoxy compound of the formula (II) present in this solution is hydrogenated in the presence of a molybdenum- and/or aluminium- and/or iron-doped sponge metal catalyst based on nickel with hydrogen gas with ring closure to give the benzoxazine compound of the formula (III)

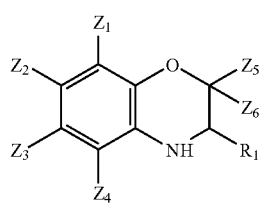

(III)

in which $R_1$ and $Z_1$ to $Z_6$ are each as defined for compounds of the formula (I), and then e) the compound of the formula (III) is reacted with an acyl halide of the formula (IV)

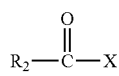

in which $R_2$ is as defined for compounds of the formula (I) and X is a halogen atom to give compounds of the formula (I).

2. Process according to claim 1, wherein, in step a), the o-nitrophenoxy carbonyl compound of the formula (II) is allowed to crystallize out of a solvent from the group of ethanol, propanol, isopropanol.

3. Process according to claim 1, wherein, in step d), the pressure of the hydrogen gas is in the range between 150 and 240 bar.

4. Process according to claim 1, wherein, in step d), the reaction temperature during the hydrogenation is between 30 and 90° C.

5. Process according to claim 1, wherein, in step c), the pH is adjusted to a value between 6 and 10.

6. Process according to claim 1, wherein the hydrogenation is performed in a solvent mixture of methanol and toluene.

7. Process according to claim 1, wherein the acyl amide compound of the formula (I) is 3,4-dihydro-3-methyl-2H-1,4-benzoxazine ($R_1$=methyl and $Z_1$ to $Z_6$ each hydrogen).

* * * * *